United States Patent [19]
Ogawa et al.

[11] Patent Number: 6,013,680
[45] Date of Patent: Jan. 11, 2000

[54] DIGESTIVE ENZYME-CONTAINING MEDICAMENT

[75] Inventors: Tomonari Ogawa; Kinya Kariya, both of Aichi; Susumu Okabe, Kyoto, all of Japan

[73] Assignee: Amano Pharmaceutical Co., Ltd., Aichi, Japan

[21] Appl. No.: 09/175,950

[22] Filed: Oct. 21, 1998

[30] Foreign Application Priority Data

Oct. 21, 1997 [JP] Japan ..................................... 9-307832

[51] Int. Cl.$^7$ .................................................. A61K 31/415
[52] U.S. Cl. ........................ 514/925; 514/926; 514/927; 514/385
[58] Field of Search ..................... 514/925, 926, 514/927, 385

[56] References Cited

U.S. PATENT DOCUMENTS

| | | | |
|---|---|---|---|
| 5,417,980 | 5/1995 | Goldman et al. | 514/927 |
| 5,618,564 | 4/1997 | Kimura et al. | 424/653 |
| 5,620,964 | 4/1997 | Roth et al. | 514/53 |
| 5,866,128 | 2/1999 | Gevas et al. | 424/184.1 |

*Primary Examiner*—James H. Reamer
*Attorney, Agent, or Firm*—Sughrue, Mion, Zinn Macpeak & Seas, PLLC

[57] ABSTRACT

To provide a medicament that can be used as a drug for the effective treatment of gastric ulcers, duodenal ulcers and like diseases of the digestive tract. The medicament comprises a combination of at least one agent selected from the group consisting of histamine $H_2$ receptor antagonists and proton pump inhibitors, and a digestive enzyme.

9 Claims, 16 Drawing Sheets

DIGESTIVE ENZYME-CONTAINING MEDICAMENT

FIELD OF THE INVENTION

This invention relates to a medicament which contains a digestive enzyme. More particularly, it relates to a medicament comprising a histamine $H_2$ receptor antagonist ("$H_2$ blocker" hereinafter) and/or a proton pump inhibitor ("PPI" hereinafter) together with a digestive enzyme. The medicament of the present invention can be used as a drug for the effective treatment of gastric ulcer, duodenal ulcer and like diseases of the digestive tract.

BACKGROUND OF THE INVENTION

Gastric and duodenal ulcers are diseases of the digestive tract which are induced by various causes such as mental stress, eating habits and intake of stimulative drinks and food. These diseases are caused by the autolysis of the mucous membranes of the digestive tract with gastric juices and are generally referred to as peptic ulcers. Peptic ulcers are caused by the increase of gastric acid, pepsin and like causative factors, and by the inability to prevent the increase of these factors due to the weakening of the body's defense mechanisms.

Examples of pharmaceutical preparations to be used in the treatment of gastric and duodenal ulcers, through the inhibition of the causative factors include an antacid which neutralizes gastric acid, an anti-pepsin agent, a gastric mucosa protecting agent, an anticholinergic drug which inhibits secretion of gastric acid, a parasympatholytic drug, an $H_2$ blocker, a PPI, and like factors.

The aforementioned $H_2$ blocker used frequently in recent years as a therapeutic drug for treatment of ulcers inhibits the secretion of hydrochloric acid and pepsin from gastric juice-secreting cells. As a result, autolysis in the stomach is inhibited and a therapeutic effect achieved. The aforementioned PPI inhibits the proton pump (($H^+ + K^+$)-ATPase) and thus exerts a wider range of inhibiting action against various stimulants of acid secretion than $H_2$ blockers.

In order to obtain a greater therapeutic effect, the $H_2$ blocker and/or the PPI has been combined together or prescribed together with an antacid such as magnesium oxide, aluminum hydroxide, magnesium hydroxide, magnesium tri-silicate, magnesium carbonate or sodium citrate.

In general, ingested food is digested via a complex process. As a general rule, ingested food is first hydrolyzed by α-amylase secreted from the salivary glands. Next, in the stomach it is digested by pepsin under acidic conditions in the presence of hydrochloric acid. Thereafter, in the intestines it is digested by various enzymes secreted from the pancreas. Finally, the nutritive components are absorbed by the digestive tract wall.

When an Hz blocker or PPI is used for the purpose of treating ulcers, the secretion of hydrochloric acid and pepsin is inhibited so that the digestive functions of the stomach become greatly inhibited. Autolysis of the gastric wall by gastric juices is the main cause of ulcers as described above. Thus, digestion of food in the stomach is greatly inhibited during such treatment of ulcers using an $H_2$ blocker or PPI.

However, it is necessary to maintain the proper conditions for absorption of nutritive components for the purpose of recovering from diseases of the digestive tract induced by various causes such as mental stress and the like. Thus, it is important to carry out the treatment of diseases of the digestive tract under conditions where the natural mechanism for digestion in the living body can be maintained at its optimum.

According to certain studies conducted by the inventors of the present invention, it was found that digestion of food with gastric juices in the living body promotes subsequent digestion with pancreatic juices and, also, enhances absorption of nutritive components by the digestive tract. Thus, such results confirm that the process involved in the digestion of food in the stomach is a markedly important process of the digestive system of the living body. Consequently, much concern has been directed toward the development of a method by which the normal gastric digestion of food can be maintained and the inhibition of digestive functions by an $H_2$ blocker or PPI can be prevented without diminishing the therapeutic effect of the $H_2$ blocker or PPI in treating ulcers.

SUMMARY OF THE INVENTION

With the aim of resolving the aforementioned problems, the inventors of the present invention have conducted intensive studies and developed the invention as a result of their efforts. The present invention provides a medicament which can maintain normal digestion in the stomach and prevent the inhibition of such digestive functions by an $H_2$ blocker or PPI, through the joint use of an $H_2$ blocker and/or PPI with a digestive enzyme which functions in the stomach. In addition, since the pH value in the stomach is increased by an $H_2$ blocker or PPI, activities of various digestive enzymes which show insufficient actions at the normal gastric pH can be improved.

Since peptic ulcer is induced by the autolytic action of gastric juices, it has been hypothesized that the action of digestive enzymes, particularly a protease, in the stomach would cause a worsening of the ulcer. However, according to the studies conducted by the present inventors, it was unexpectedly found that the digestion of food in the stomach can be carried out without a worsening of the ulcer when a digestive enzyme specified in the present invention is used so that absorption of nutritive components from the digestive tract can be enhanced.

The present invention is a medicament in which at least an $H_2$ blocker and/or PPI together with a digestive enzyme are used in combination as active ingredients. The medicament of the present invention exerts a therapeutic effect on ulcers and can maintain the normal digestive function of food in the stomach and, also, prevent the inhibition of the digestive functions of the stomach by $H_2$ blocker or PPI used alone.

DETAILED DESCRIPTION OF THE INVENTION

Figure 1:
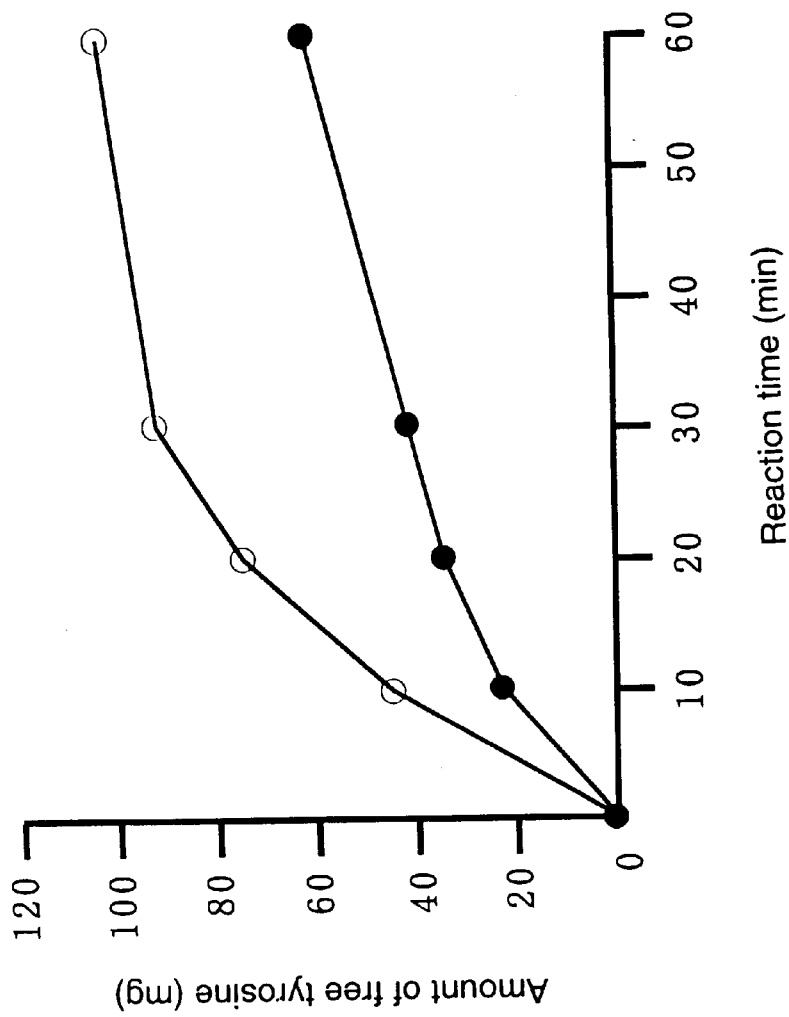
FIG. 1 is a graph showing results of Test Example 1, in which -o- shows a value obtained by subtracting the amount of free tyrosine when pepsin was used alone from the amount of free tyrosine when pepsin and pancreatin were used in combination.

Examples of the $H_2$ blocker to be used in the present invention include cimetidine, ranitidine, famotidine and like $H_2$ blockers. These compounds can be used alone or in a combination of two or more. The amount of the $H_2$ blocker used in the present invention is not particularly limited. For example, cimetidine, ranitidine, and famotidine may be used generally in a dose of from 400 to 800 mg/day, 150 to 300 mg/day, and 20 to 40 mg/day, respectively. More than half or less than twice the amount in the above range may also be used.

Examples of the PPI to be used in the present invention include omeprazole, lansoprazole, and raveprazole. These compounds can be used alone or in a combination of two or more. The amount of the PPI used in the present invention is not particularly limited. For example, the PPI may be used generally in a dose from 20 to 60 mg/day. More than half or less than twice the amount in the above range may also be used.

With regard to the digestive enzyme to be used jointly with the $H_2$ blocker and/or PPI described above, any digestive enzyme can be used with the proviso that it is a digestive enzyme that can react at a gastric pH value caused by the administration of the $H_2$ blocker or PPI and, also, can digest food under such conditions without worsening the ulcerated region.

When an $H_2$ blocker or PPI is used, the pH value in the stomach increases generally in the range of pH 4 to 6. In addition, when an antacid or the like is jointly used, the pH value further increases and reaches a value of pH 6 or greater for a short period of time. Consequently, the enzyme which can be used depends on the pH that results when the pharmaceutical preparation is applied. Various commercially available digestive enzymes can be used in the medicament.

There are various enzymes that originate from animals, plants and microorganisms as commercially available digestive enzymes for medical use, but microbial enzymes are suitably used in the present invention. For example, with regard to the specific types of enzymes, a starch hydrolyzing enzyme, a protein hydrolyzing enzyme, a fat hydrolyzing enzyme, a fiber hydrolyzing enzyme and like digestive enzymes and, also, multiple digestive enzyme system in which these enzymes are combined can be used. In view of the aspect of the present invention to restore the digestive functions inhibited by an $H_2$ blocker or PPI, proteases are preferably used. As the protease, any enzymes having an protease activity can be used without particular limitation. Further examples include Biodiastase, Biodiastase 500, Biodiastase 700, Biodiastase 1000, Biodiastase 2000, Newlase, Prozyme, Prozyme 6, Lipase AP4, Lipase AP6, Lipase AP12, Lipase Mi-AP5, Lipase M-AP10, Lipase M-AP20, Cellulase AP, Cellulase AP3, Cellulase T-AP2, Cellulase T-AP4, Cellulase T-AP6, Pancreatic Digestive Enzyme TA and Pancreatic Digestive Enzyme 8AP (mfd. by Amano Pharmaceutical), Biotamylase, Biotamyolase S, Biotalase A-1000, Biotalase P-1000 and Denapsin 10 (mfd. by Nagase Biochemicals), Cellulosine AP and Prolisin (mfd. by Ueda Chemical), Lipase Saiken (mfd. by Osaka Bacterial Research Laboratory), Takadiastase (mfd. by Sankyo), Sumizyme (mfd. by Shin Nippon Chemical Industry), Biotamylase (mfd. by Nagase), Lipase MY (mfd. by The Meito Sangyo) and like digestive enzymes. More preferably, Prozyme 6 as a protease, Biodiastase 2000 as a multiple digestion enzyme system and like digestive enzymes and enzyme systems can be used.

The amounts of the digestive enzymes to be used are not particularly limited, with the proviso that they are able to exert sufficient digestive activity in the stomach when formulated. However, as an example, the following formulation standard (for medical use) can be generally used as pharmaceutical preparations.

When the digestion activity is expressed in accordance with the digestion activity test method provided for in the general test methods of *The 13th Revision of Japanese Pharmacopoeia*, the dose per single administration is:

1) 197 units or more for the starch digestion activity;

2) 15,000 units or more for the protein digestion activity; and 3) 300 units or more for the fat digestion activity.

In addition, these activity units become the following values when measured in accordance with the United States Pharmacopeia (USP) method or Federation International Pharmaceutique (FIP) method.

Starch digestion activity: USP method=about 2,200 units or more FIP method=about 556 units or more Protein digestion activity: USP method=about 12,500 units or more FIP method=about 200 units or more Fat digestion activity: USP method=about 1,600 units or more FIP method=about 2,100 units or more.

More than half or less than twice the activity in the above may also be used as long as the effects are expected.

According to the present invention, an $H_2$ blocker and/or a PPI together with a digestive enzyme are used by administering them in combination to the living body. Further, they may be made into separate pharmaceutical preparations and used in combination thereof, or the $H_2$ blocker and/or PPI and the digestive enzyme may be used simultaneously by making them into a single pharmaceutical preparation. In making these pharmaceutical preparations, other active ingredients may be combined with the preparation as the circumstances demand taking into consideration problems of incompatibility between the active ingredients and also the need to maintain the digestive functions of the stomach. As a matter of course, various alternative active ingredients may be combined with the pharmaceutical preparation for the formulation. For example, a digestive enzyme together with an $H_2$ blocker or PPI may be used as a medicament by further combining them with an antacid.

These pharmaceutical compositions can be provided in various dosages. As described above, a medicament can be produced in such a form that a pharmaceutical preparation of an $H_2$ blocker or PPI, and a pharmaceutical preparation of a digestive enzyme separately prepared, are simultaneously taken in combination. Also, a medicament can be produced by combining these active ingredients into a single pharmaceutical preparation. These medicaments can be made in all the usual forms of commercially available medicaments such as liquids, capsules, granules, pills, suspensions, emulsions, powders, tablets, syrups, lemonades and the like, with the proviso that the active ingredients combined therein maintain their efficacy.

The following Test Examples and Examples are provided to further illustrate the present invention. However, the invention is not limited to these examples and encompasses aspects of the invention that one skilled in the art can deduce from the disclosed examples.

Test Example 1: Confirmation of the importance of gastric digestion in a digestive tract model using mixed substrates (1) Method The substrate solution used herein was prepared by adding 1.8% bovine serum albumin, 6.7% starch hydrolysate (PINE-DEX #100, mfd. by Matsutani Chemical), 2.7% olive oil, 0.1% gastric mucosa mucin, 150 mM NaCl and 1 mM $CaCl_2$ to an acetate buffer and then adjusting the resulting solution to pH 4.0 with hydrochloric acid.

A 140 ml aliquot of the substrate solution was kept at 37° C. and gently stirred while adding thereto 10 ml of 0.2% pepsin solution or 10 ml of water to carry out the reaction, 4 ml of 0.2N hydrochloric acid was added to the aliquot 5 minutes after the commencement of the reaction and then, until 70 minutes thereafter, 4 ml of 0.2N hydrochloric acid was added at an interval of 15 minutes. A period up until 120 minutes after the reaction was used as the simulated gastric environment. A simulated intestinal environment was prepared thereafter by adding 3.0 g of sodium bicarbonate, 0.31 g of sodium taurodeoxycholate and 150 mg of Pancreatic Digestive Enzyme 8AP (a high potency pancreatin, mfd. by Amano Pharmaceutical) to the reaction solution. The activity was obtained by taking out sample aliquots during the reaction, stopping the reaction by adding trichloroacetic acid to the sample aliquots and then measuring the amount of free tyrosine in the resulting supernatant fluid of the sample aliquots by the Folin method. The relationship between the reaction time in the simulated gastric environment and the amount of tyrosine is shown in FIG. 1.

(2) Results

In FIG. 1, -o- shows a result obtained by subtracting the amount of free tyrosine when pepsin was solely used from the amount of free tyrosine when pepsin and pancreatin were used, and -●- shows the amount of free tyrosine when pancreatin was solely used. The amount of free tyrosine is indicative of the amount of protein digestion.

Thus, as is evident from the results, digestion of protein by pancreatin is considerably enhanced when pepsin is first added and then pancreatin is allowed to exert its digestive action, in comparison with the other case in which only pancreatin is allowed to exert its action without adding pepsin.

TABLE 1

| | Amount of free tyrosine (mg) | | | |
|---|---|---|---|---|
| Reaction time (min) | Pepsin (A) | Pepsin + pancreatin (B) | Pancreatin only | B − A |
| 0 (gastric environment) | 56.32 | 56.32 | 0 | 0 |
| 10 (intestinal environment) | 56.32 | 101.09 | 25.71 | 44.77 |
| 20 (intestinal environment) | 56.32 | 131.34 | 37.17 | 75.02 |
| 30 (intestinal environomnet) | 56.32 | 147.11 | 43.67 | 90.79 |
| 60 (intestinal environment) | 56.32 | 158.44 | 63.91 | 102.12 |

On the basis of these results, it was revealed that digestion of ingested food in the stomach with pepsin markedly accelerates further digestion of the ingested food with pancreatin present in the pancreatic juice and, thus, resulted in the finding that the digestion of food in the stomach is important for the effective functioning of the pancreatic system.

Test Example 2: Examination of the effect of digestive enzymes on gastric ulcer (1) Method Digestive enzymes (Biodiastase 2000 (an amylase preparation) and Prozyme 6 (a protease preparation), both manufactured by Amano Pharmaceutical) were dissolved in water. The rats having a kissing gastric ulcer (an example of a rat chronic gastric ulcer model) were formed by injecting acetic acid into the rat stomach.

After three times a day for two weeks of continuous oral administration of the enzymes, the effect of the enzymes on the gastric ulcer region was compared with that of a control group that was not treated with the enzymes.

Figure 2:
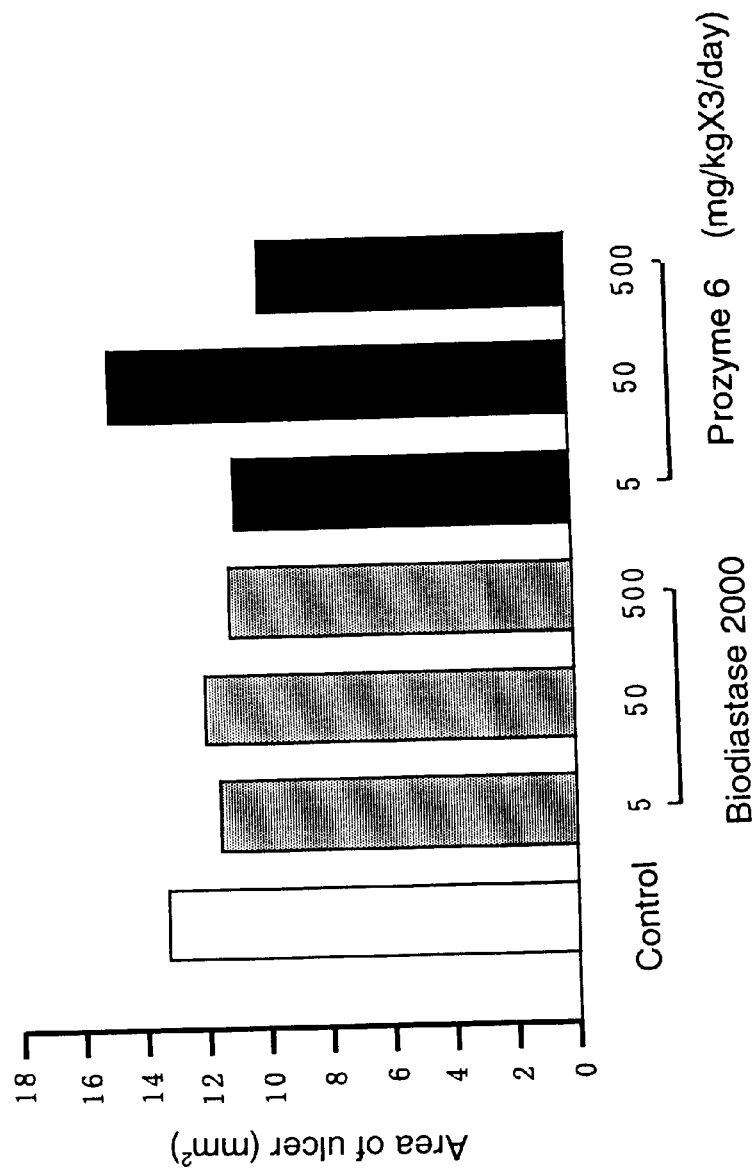
FIG. 2 is a graph showing results of Test Example 2, indicating that the ulcer region is not affected by the use of various digestive enzyme preparations.

The dosage of each digestive enzyme was set as follows.
Biodiastase 2000: 5 mg/kg, 50 mg/kg and 500 mg/kg (per dose)
Prozyme 6: 5 mg/kg, 50 mg/kg and 500 mg/kg (per dose)
The results are shown in FIG. 2.

Figure 3:
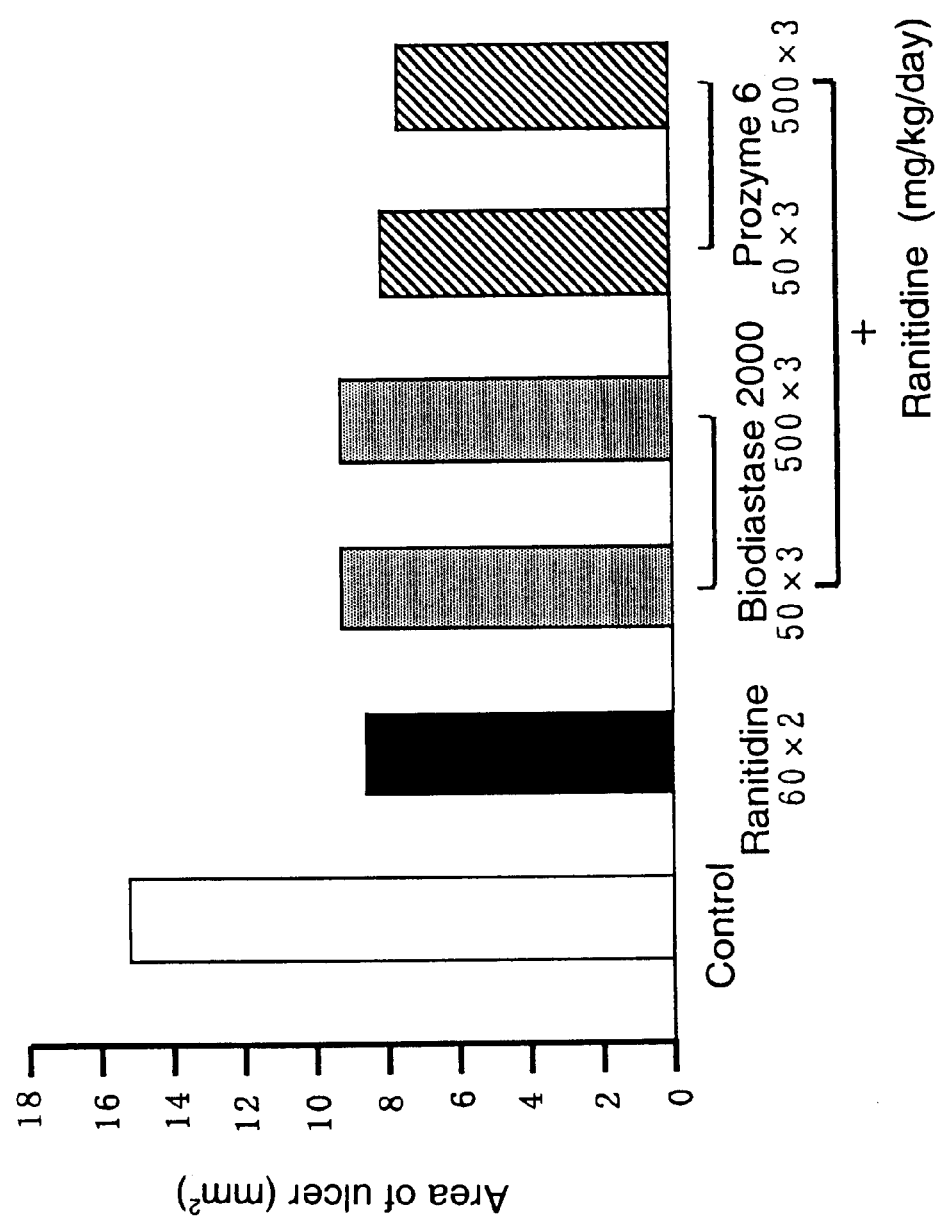
FIG. 3 is a graph showing results of Test Example 2, indicating that the therapeutic effect is not affected when an $H_2$ blocker is used in combination with an enzyme preparation.
Figure 4:
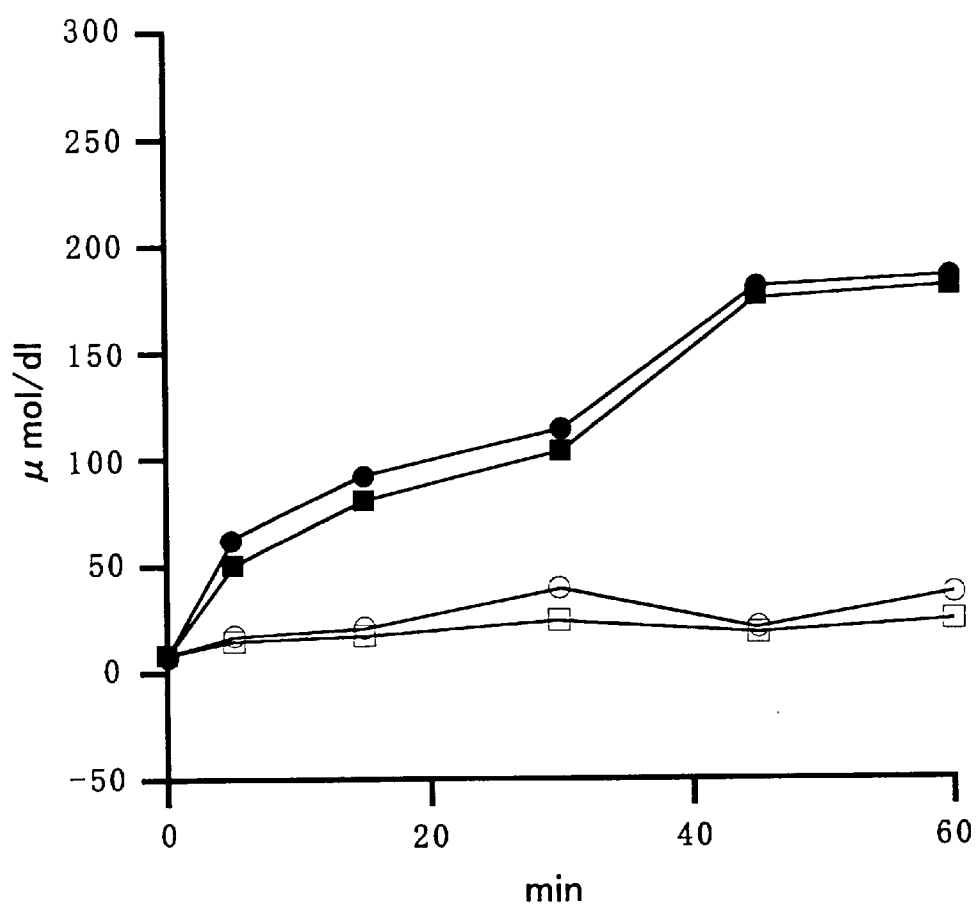
FIG. 4 is a graph showing results of the alanine measurement of Test Example 3, in which -o- shows the result of Group 1, -●- shows the result of Group 2, -□- shows the result of Group 3, and -■- shows the result of Group 4.
Figure 5:
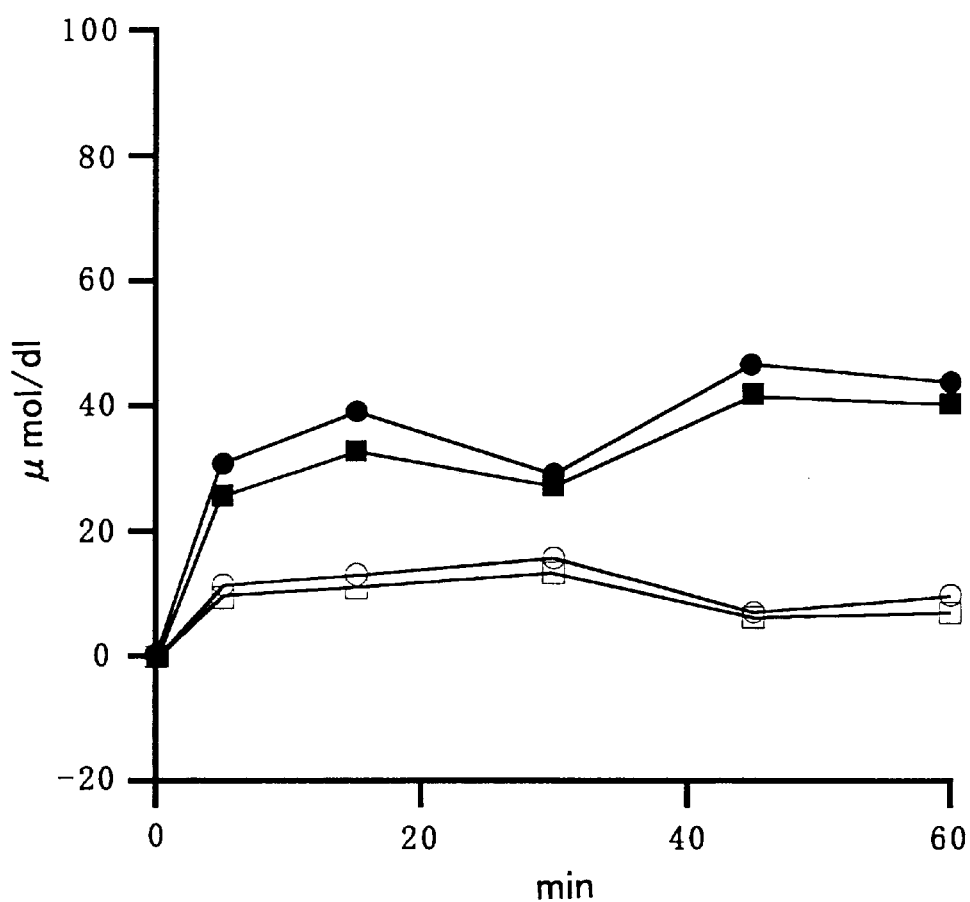
FIG. 5 is a graph showing results of the threonine measurement of Test Example 3, in which -o- shows the result of Group 1, -●- shows the result of Group 2, -□- shows the result of Group 3, and -■- shows the result of Group 4.
Figure 6:
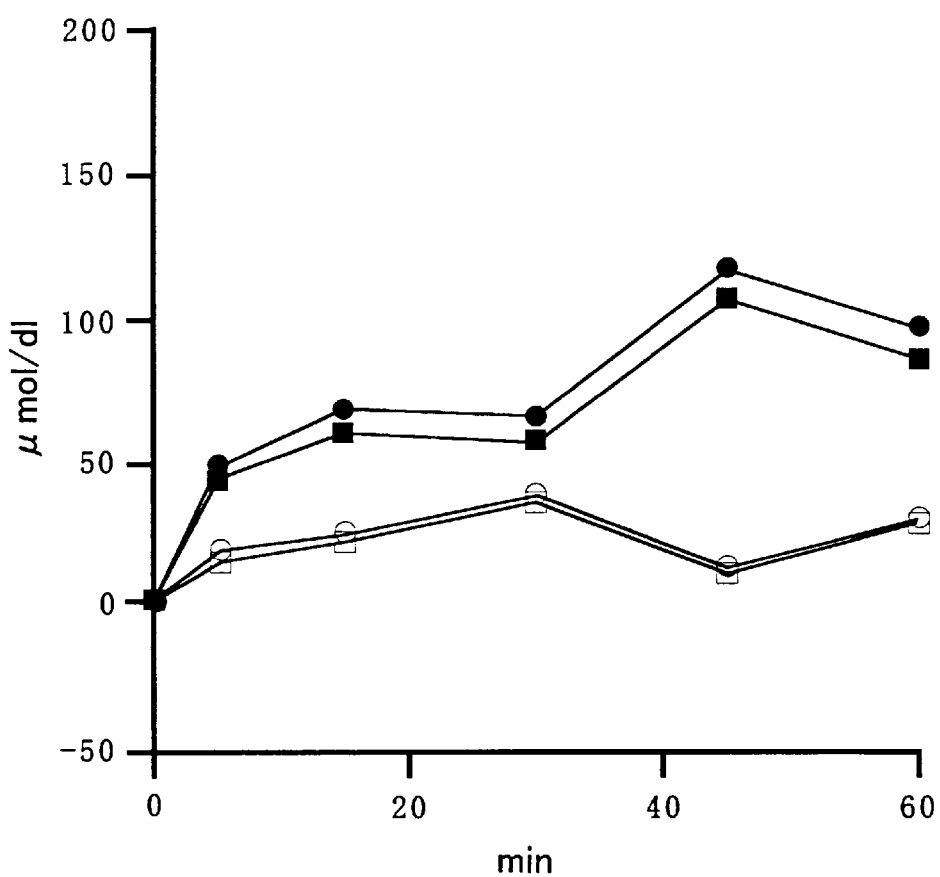
FIG. 6 is a graph showing results of the lysine measurement of Test Example 3, in which -○- shows the result of Group 1, -●- shows the result of Group 2, -□- shows the result of Group 3, and -■- shows the result of Group 4.
Figure 7:
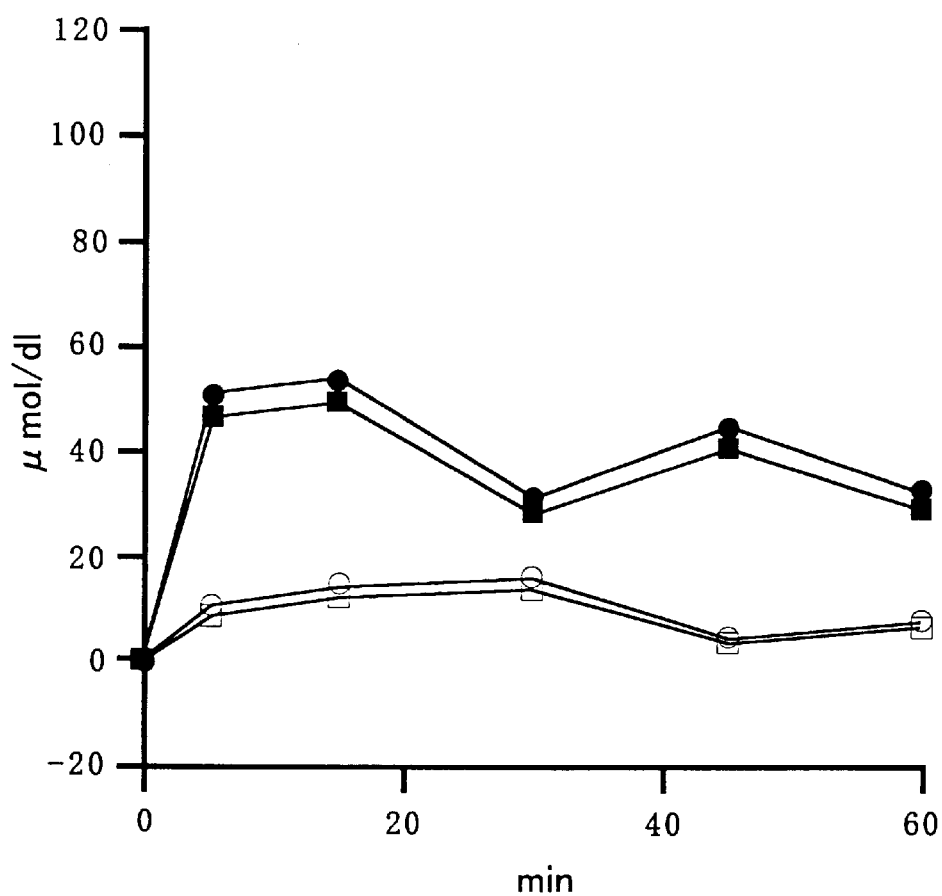
FIG. 7 is a graph showing results of the valine measurement of Test Example 3, in which -○- shows the result of Group 1, -●- shows the result of Group 2, -□- shows the result of Group 3, and -570 - shows the result of Group 4.
Figure 8:
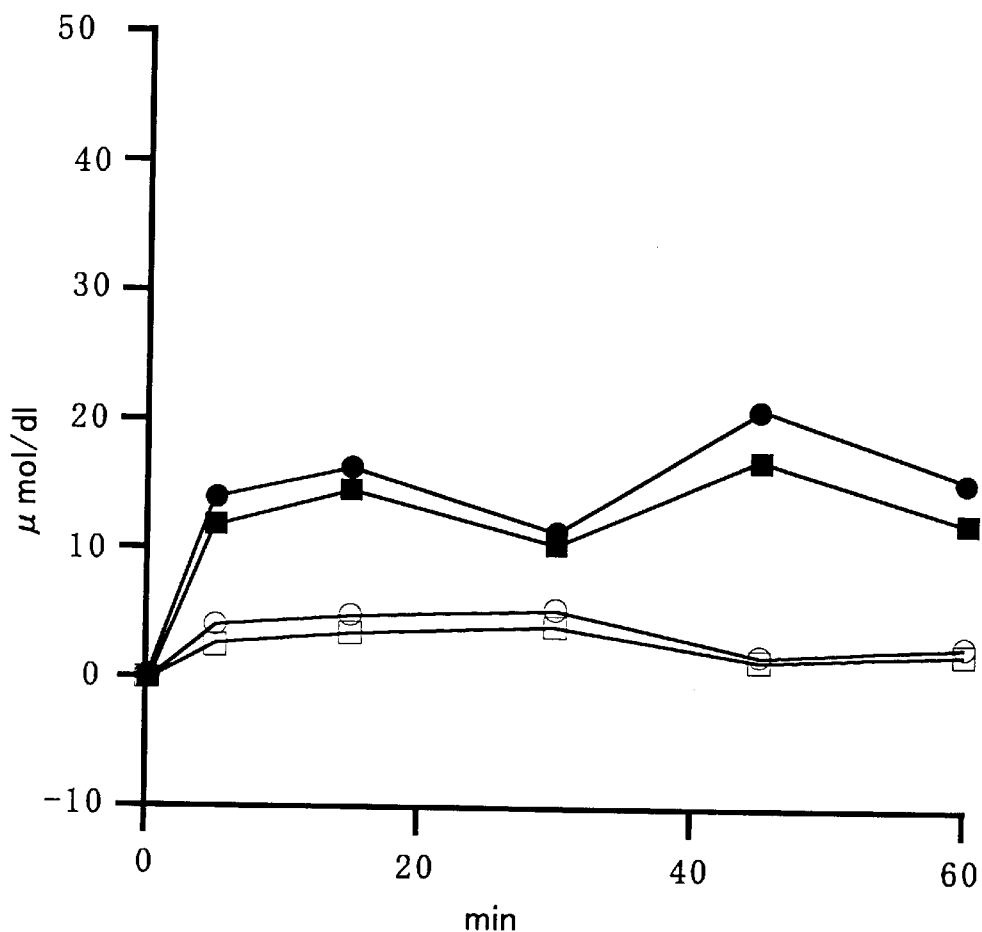
FIG. 8 is a graph showing results of the isoleucine measurement of Test Example 3, in which -○- shows the result of Group 1, -●- shows the result of Group 2, -□- shows the result of Group 3, and -■- shows the result of Group 4.
Figure 9:
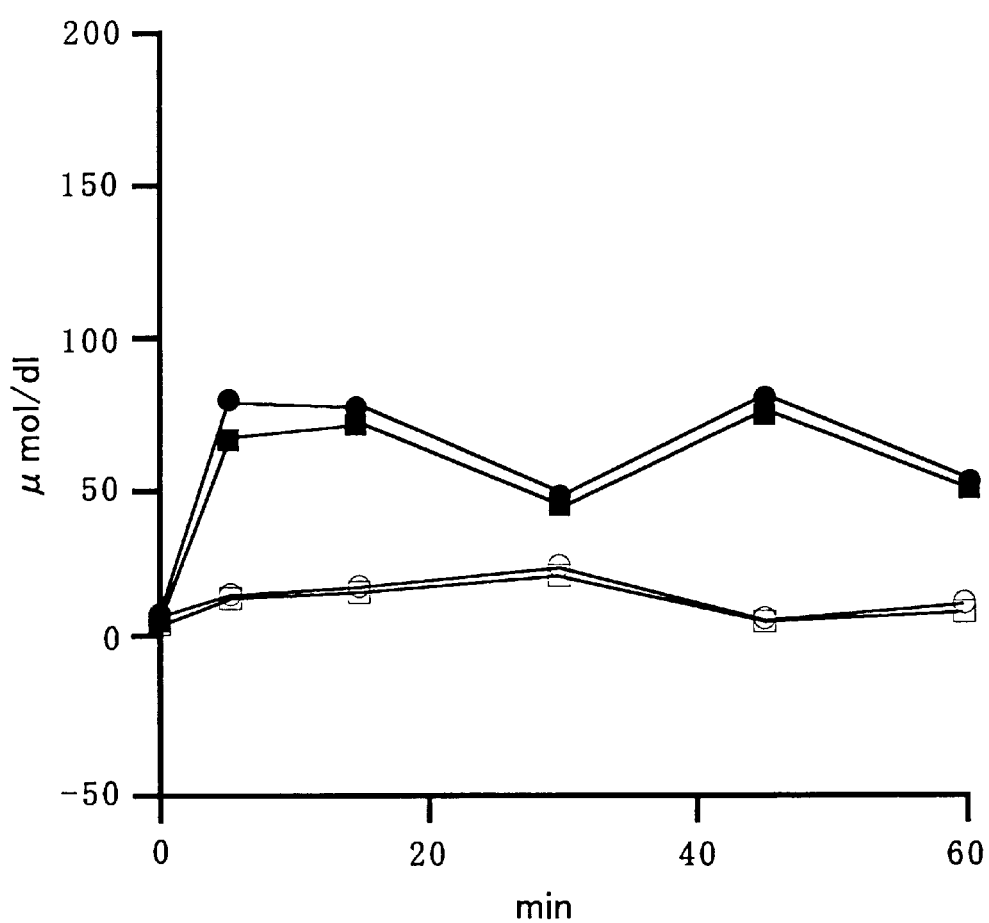
FIG. 9 is a graph showing results of the leucine measurement of Test Example 3, in which -○- shows the result of Group 1, -●- shows the result of Group 2, -□- shows the result of Group 3, and -■- shows the result of Group 4.

Also, an $H_2$ blocker (ranitidine) used as a drug for treatment of ulcers was suspended in 0.5% CMC and orally administered at a dosage of 60 mg/kg twice a day in order to examine the effect of the joint use of the $H_2$ blocker with the digestive enzymes. The dosage of each digestive enzyme was set as follows.
Biodiastase 2000: 50 mg/kg and 500 mg/kg (per dose)
Prozyme 6: 50 mg/kg and 500 mg/kg (per dose)
The results are shown in FIG. 3.

After two weeks of continuous oral administration of these drugs, the rats were forced to undergo 18 hours of fasting. Thereafter, the gastric contents of each rat were recovered by pyloric ligation, and the stomach was incised along its greater curvature to measure, under a microscope, the area ($mm^2$) where ulcers had developed on the anterior and posterior walls.

(2) Results

As is evident from the results shown in FIG. 2, two weeks of continuous administration of the digestive enzymes (an amylase preparation and a protease preparation) showed no significant difference when compared to the control group having untreated acetic acid-induced gastric ulcers, thus revealing that these enzymes do not worsen the ulcer.

Also, as is evident from the results shown in FIG. 3, when the $H_2$ blocker was used alone or in combination with the digestive enzymes, a significant healing effect on the acetic acid-induced ulcer was observed in both cases. On the basis of these results, it was revealed that these digestive enzymes do not act as a factor that worsens the ulcers.

Test Example 3: Influence of proteases on amino acid absorption (1) Method

Under pentobarbital anesthetization, seven-week-old Wistar/ST male rats (208.7 to 243.2 g purchased from Nippon SLC) were subjected to cannulation at the portal vein and the superior vena cava. The rats were individually kept in a cage for 24 hours while fasting. Then, purified water (control group) or famotidine (0.33 mg/5 ml/kg) was orally administered and, after 30 minutes, bovine serum albumin (BSA) (1.3 g/10 ml/kg) as a substrate was orally administered. Thereafter, Prozyme 6 (60 mg/5 ml/kg) was orally administered. An enzyme solution containing MgO was administered to the group that received famotidine. After 51 15, 30, 45 and 60 minutes after the administration of BSA, 0.2 ml of blood was collected from each rat, from the portal vein and the superior vena cava. The blood was subjected to centrifugation at 3000 rpm for 15 minutes to obtain plasma.

The plasma (50 μas diluted with an internal standard solution to 20 ml. An aliquot of the resulting solution was used for amino acid analysis (4-fluoro-7-nitrobenzofuran (NBD-F): the precolumn method). The concentration of each amino acid was calculated by subtracting the amino acid concentration of the superior vena cava blood from the amino acid concentration of the portal vein blood. The individual groups and the ingredients administered to each group were as follows.

Group 1: purified water+heat-inactivated Prozyme 6
Group 2: purified water+Prozyme 6
Group 3: famotidine+magnesium oxide+heat-inactivated Prozyme 6
Group 4: famotidine+magnesium oxide+Prozyme 6

The results are shown in FIGS. 4 to 9.

administered as a substrate, and subsequently, 60 mg/5 ml/kg of Prozyme 6 was orally administered. In this case, an enzyme solution containing magnesium oxide was administered to the group that received cimetidine. Thermally inactivated Prozyme 6 (heated for 20 minutes in boiling water) was administered to the control group. After 15 minutes and 30 minutes of administration of BSA, each rat was anesthetized with ether and the stomach of the rat excised.

The gastric contents of the excised stomach were then transferred to a centrifugation tube and suspended in purified water. The contents in the centrifugation tube were then mixed with 5 ml of 20% trichloroacetic acid (TCA). The mixture was allowed to stand for 30 minutes in an ice bath and was then centrifuged at 3,000 rpm for 20 minutes. The amount of protein in the resulting supernatant fluid, namely the TCA soluble fraction, was measured by the Folin method. The results 15 minutes and 30 minutes after the enzyme preparation was administered are summarized in Table 2 and Table 3, respectively. The gastric digestion ratio was calculated based on the following formula.

(Residual digests in the stomach/BSA administered)×100

TABLE 2

|  | Group 1 | Group 2 | Group 3 | Group 4 |
| --- | --- | --- | --- | --- |
| Number of rats | 6 | 6 | 6 | 6 |
| Dosage (mg) | 254.4 ± 6.8 | 252.8 ± 9.2 | 255.1 ± 8.3 | 252.9 ± 5.6 |
| Residue in the stomach (mg) | 84.3 ± 30.6 | 88.5 ± 20.9 | 88.5 ± 19.6 | 114.0 ± 36.5 |
| Digested (mg) | 18.2 ± 6.3 | 33.5 ± 8.7** | 14.0 ± 3.4 | 31.8 ± 9.8* |
| Un-digested (mg) | 66.1 ± 27.2 | 55.0 ± 15.2 | 74.5 ± 18.8 | 82.2 ± 27.4 |
| Gastric digestion ratio (%) | 7.2 ± 2.5 | 13.3 ± 3.4** | 5.5 ± 1.3 | 12.6 ± 3.9* |
| Gastric pH | 4.6 ± 0.6 | 4.7 ± 0.5 | 5.3 ± 0.5 | 5.3 ± 0.5 |

TABLE 3

|  | Group 1 | Group 2 | Group 3 | Group 4 |
| --- | --- | --- | --- | --- |
| Number of rats | 6 | 6 | 6 | 6 |
| Dosage (mg) | 252.5 ± 6.4 | 255.4 ± 11.6 | 257.7 ± 9.0 | 255.3 ± 3.7 |
| Residue in the stomach (mg) | 72.4 ± 22.8 | 101.2 ± 29.4 | 85.2 ± 26.1 | 120.7 ± 36.5 |
| Digested (mg) | 30.2 ± 7.8 | 51.9 ± 13.3** | 20.8 ± 3.1* | 50.2 ± 15.0* |
| Un-digested (mg) | 42.2 ± 19.3 | 49.4 ± 19.0 | 64.4 ± 23.9 | 70.5 ± 21.8* |
| Gastric digestion ratio (%) | 12.0 ± 3.1 | 20.4 ± 5.6** | 8.1 ± 1.1* | 19.6 ± 5.7* |
| Gastric pH | 3.5 ± 0.8 | 4.7 ± 0.5* | 5.0 ± 0.6** | 5.2 ± 0.5** |

(2) Result

As is evident from the figures, blood concentrations of various amino acids were increased over time by the use of protease, without any inhibiting effect by the administration of $H_2$ blocker.

Example 1: Joint use of an $H_2$ blocker with a protease (1)

(1) Method

Purified water or cimetidine (5 mg/5 ml/kg) was administered to seven-week-old Wistar/ST male rats (186.0 to 208.5 g) which were forced to undergo 24 hours of fasting. 30 minutes thereafter, 1.3 g/10 ml/kg of BSA was orally The individual groups and the ingredients administered to each group in Tables 2 and 3 are as follows.

Group 1: purified water+heat-inactivated Prozyme 6
Group 2: purified water+Prozyme 6
Group 3: cimetidine+magnesium oxide+heat-inactivated Prozyme 6
Group 4: cimetidine+magnesium oxide+Prozyme 6

Figure 10:
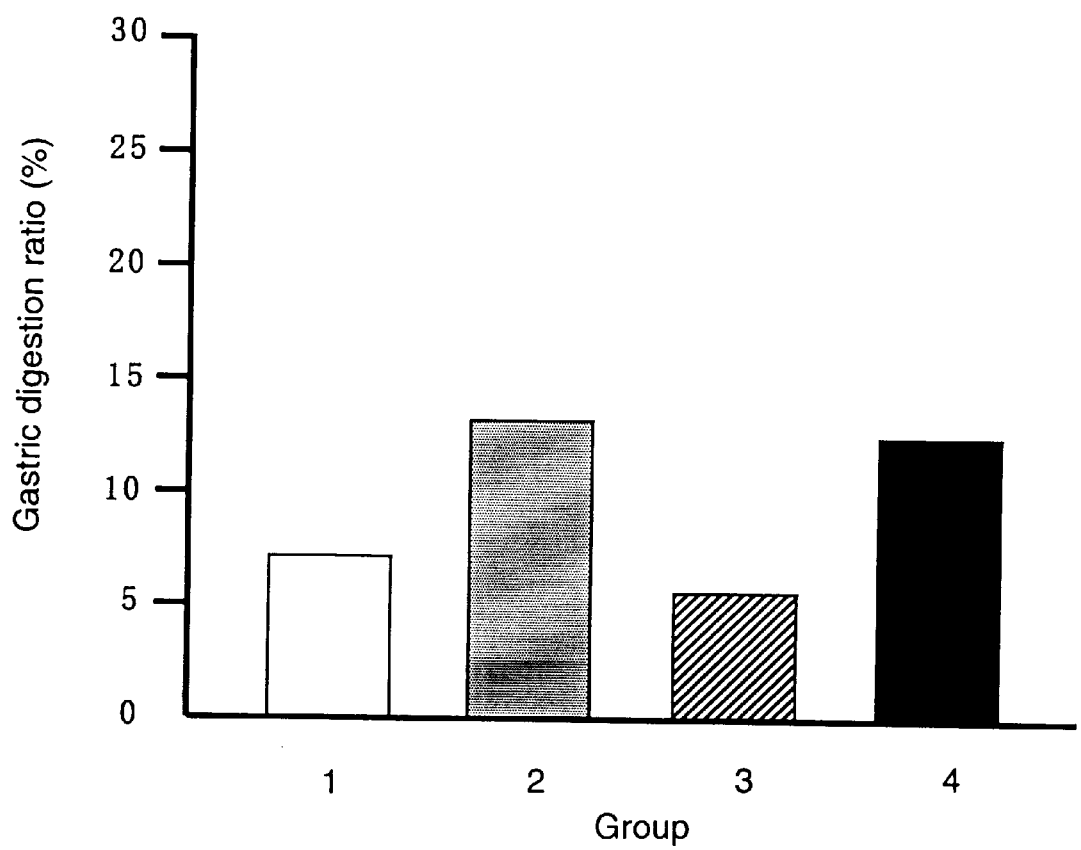
FIG. 10 is a graph showing results after 15 minutes of administration in Example 1.
Figure 11:
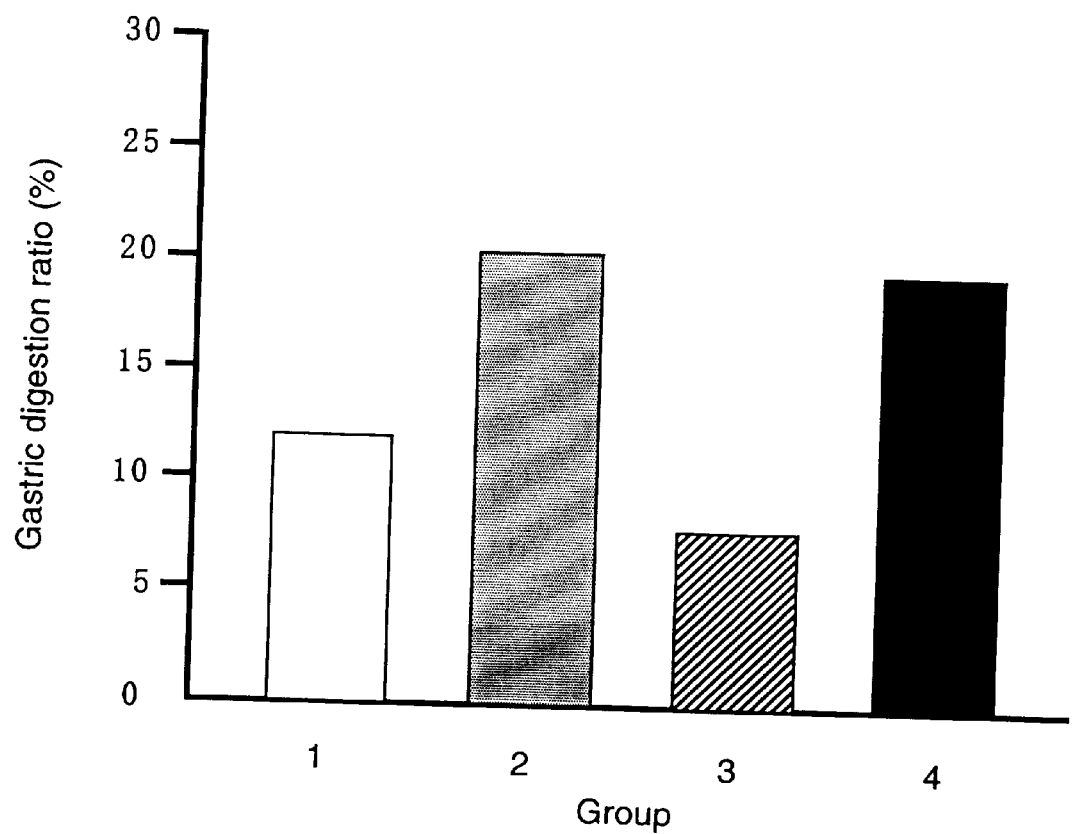
FIG. 11 is a graph showing results after 30 minutes of administration in Example 1.

The symbol ** indicates significant difference at P<0.01, and * significant difference at P<0.05. The results 15 minutes and 30 minutes after the enzyme preparation was administered are shown in FIG. 10 and FIG. 11, respectively.

(2) Results

As is evident from the figures, in comparison with the control groups, digestion in the stomach is significantly enhanced by the administration of Prozyme 6 alone after both 15 minutes and 30 minutes of the administration of the BSA. When cimetidine alone was administered, a decreasing tendency or significant decrease in the gastric digestion was observed in comparison with the control groups. The effect seems to be due to the inhibition of digestion by pepsin in the stomach caused by the administration of cimetidine. On the other hand, when cimetidine and Prozyme 6 were used in combination, digestion in the stomach was significantly accelerated in comparison with the group in which cimetidine alone was administered. Further, the inhibition of digestion caused by the cimetidine was prevented.

Example 2: Joint use of an H, blocker with a protease (2)

The measurement of digestion was carried out in the same manner as described in Example 1, except that ranitidine was used in stead of cimetidine.

(1) Method

Purified water (control group) or ranitidine (2.5 mg/5 ml/kg) was administered to seven-week-old Wistar/ST male rats (190.5 to 207.5 g) which were forced to undergo 24 hours of fasting. 30 minutes thereafter, 1.3 g/10 ml/kg of BSA was orally administered as a substrate, and subsequently, 60 mg/5 ml/kg of Prozyme 6 was orally administered. An enzyme solution containing magnesium oxide was administered to the group that received ranitidine. After 15 minutes or 30 minutes of the BSA administration, each rat was anesthetized with ether and the stomach excised. The gastric contents of the excised stomach were transferred to a centrifugation tube and suspended in purified water. The contents in the centrifugation tube were then mixed with 5 ml of 20% trichloroacetic acid (TCA). The mixture was allowed to stand for 30 minutes in an ice bath and was then centrifuged at 3,000 rpm for 20 minutes. The amount of protein in the resulting supernatant fluid, namely the TCA soluble fraction, was measured by the Folin method. The results 15 minutes and 30 minutes after the enzyme preparation was administered are summarized in Table 4 and Table 6, respectively.

Example 3: Joint use of an H, blocker with a protease (3)

The measurement of digestion was carried out in the same manner as described in Example 1, except that famotidine was used instead of cimetidine.

(1) Method

Purified water (control group) or famotidine (0.33 mg/5 ml/kg) was administered to seven-week-old Wistar/ST male rats (200.0 to 209.5 g) which were made to undergo 24 hours of fasting. 30 minutes thereafter, 1.3 g/10 ml/kg of BSA was orally administered as a substrate, and subsequently, 60 mg/5 ml/kg of Prozyme 6 was orally administered. An enzyme solution containing magnesium oxide was administered to the group that received famotidine. After 15 minutes or 30 minutes of the BSA administration, each rat was anesthetized with ether and the stomach excised. The gastric contents of the excised stomach were transferred to a centrifugation tube and suspended in purified water. The contents in the centrifugation tube were then mixed with 5 ml of 20% trichloroacetic acid (TCA). The mixture was allowed to stand for 30 minutes in an ice bath and was then centrifuged at 3,000 rpm for 20 minutes. The amount of protein in the resulting supernatant fluid, namely the TCA soluble fraction, was measured by the Folin method. The results 15 minutes and 30 minutes after the enzyme preparation was administered are summarized in Tables 4 and 5 and Tables 6 and 7, respectively.

TABLE 4

|  | Group 1 | Group 2 | Group 3 | Group 4 |
| --- | --- | --- | --- | --- |
| Number of rats | 5 | 6 | 5 | 5 |
| Dosage (mg) | 256.9 ± 8.06 | 252.8 ± 9.2 | 256.3 ± 6.76 | 258.5 ± 9.75 |
| Digests in the stomach (mg) | 19.2 ± 2.99 | 33.5 ± 8.7** | 13.5 ± 1.43** | 30.6 ± 6.50** |
| Gastric digestion ratio (%) | 7.5 ± 1.17 | 13.3 ± 3.4** | 5.3 ± 0.53** | 11.8 ± 2.55** |
| Gastric pH | 4.4 ± 0.55 | 4.7 ± 0.5 | 5.0 ± 0.00 | 5.0 ± 0.00 |

TABLE 5

|  | Group 5 | Group 6 |
| --- | --- | --- |
| Number of rats | 5 | 5 |
| Dosage (mg) | 255.9 ± 7.97 | 258.3 ± 8.05 |
| Digests in the stomach (mg) | 11.9 ± 2.02** | 30.4 ± 7.72* |
| Gastric digestion ratio (%) | 4.6 ± 0.78** | 11.7 ± 2.74* |
| Gastric pH | 5.4 ± 0.55* | 5.4 ± 0.89 |

TABLE 6

|  | Group 1 | Group 2 | Group 3 | Group 4 |
| --- | --- | --- | --- | --- |
| Number of rats | 5 | 6 | 5 | 5 |
| Dosage (mg) | 257.5 ± 9.21 | 255.4 ± 11.6 | 260.8 ± 10.4 | 261.9 ± 8.50 |
| Digests in the stomach (mg) | 26.5 ± 3.61 | 51.9 ± 13.3** | 20.7 ± 3.93* | 56.6 ± 5.13*** |
| Gastric digestion ratio (%) | 10.3 ± 1.57 | 20.4 ± 5.6** | 7.9 ± 1.53* | 21.6 ± 2.23*** |
| Gastric pH | 4.0 ± 0.71 | 4.7 ± 0.5* | 5.2 ± 0.45* | 5.2 ± 0.45* |

TABLE 7

|  | Group 5 | Group 6 |
|---|---|---|
| Number of rats | 5 | 5 |
| Dosage (mg) | 258.3 ± 5.06 | 255.7 ± 10.5 |
| Digests in the stomach (mg) | 13.9 ± 3.83*** | 40.1 ± 6.77** |
| Gastric digestion ratio (%) | 5.4 ± 1.48*** | 15.7 ± 2.67** |
| Gastric pH | 5.4 ± 0.55** | 5.6 ± 0.55** |

The individual groups and the ingredients administered to each group in Tables 4 to 7 are as follows.
  Group 1: purified water+heat-inactivated Prozyme 6
  Group 2: purified water+Prozyme 6 (data of Example 1 were used)
  Group 3: ranitidine+magnesium oxide+heat-inactivated Prozyme 6
  Group 4: ranitidine+magnesium oxide+Prozyme 6
  Group 5: famotidine+magnesium oxide+heat-inactivated Prozyme 6
  Group 6: famotidine+magnesium oxide+Prozyme 6

Figure 12:
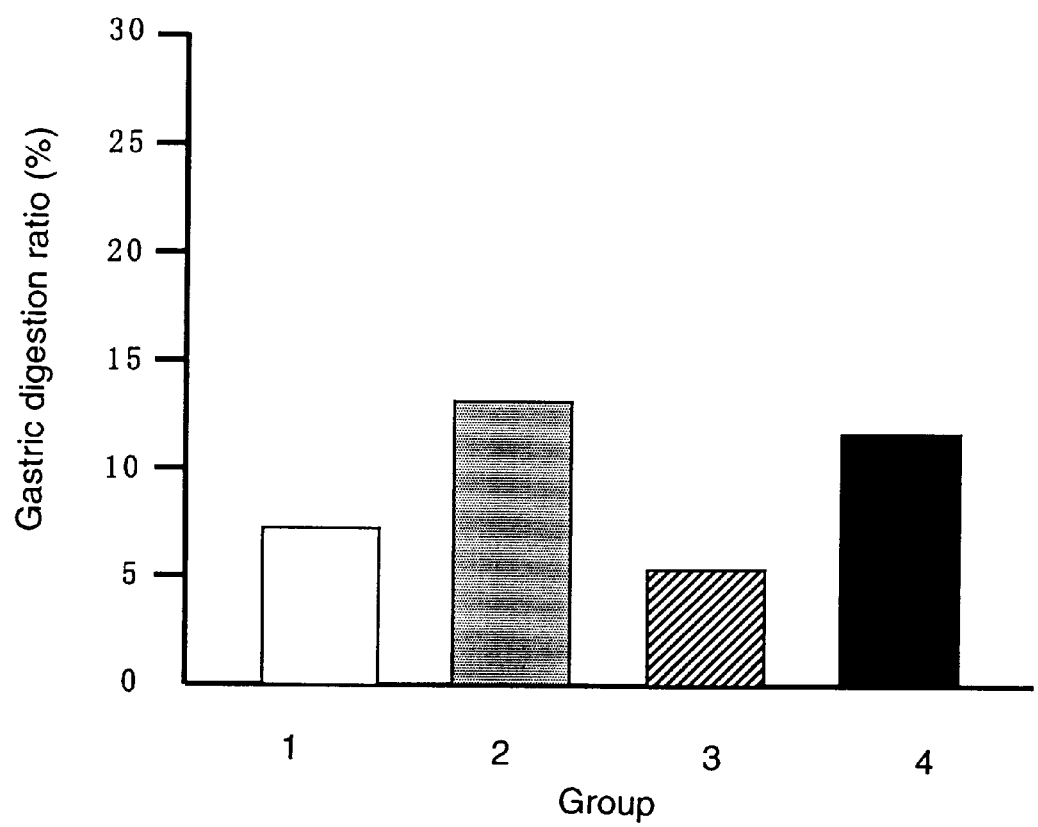
FIG. 12 is a graph showing results after 15 minutes of administration in Example 2.
Figure 13:
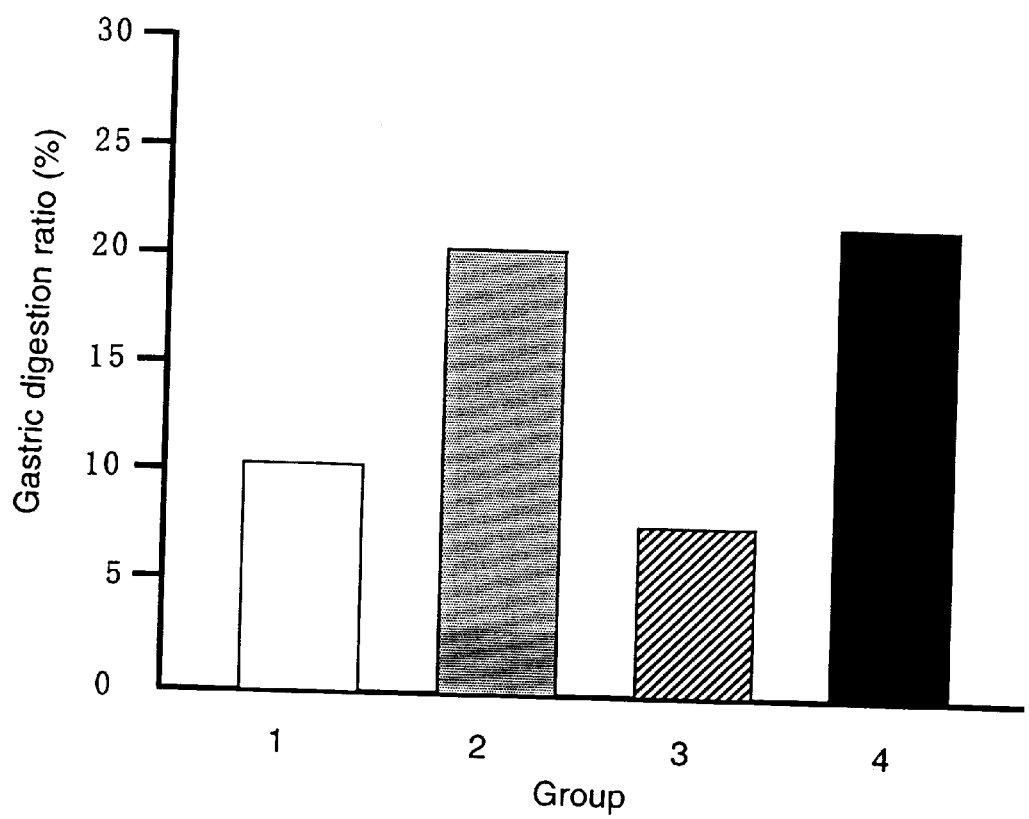
FIG. 13 is a graph showing results after 30 minutes of administration in Example 2.
Figure 14:
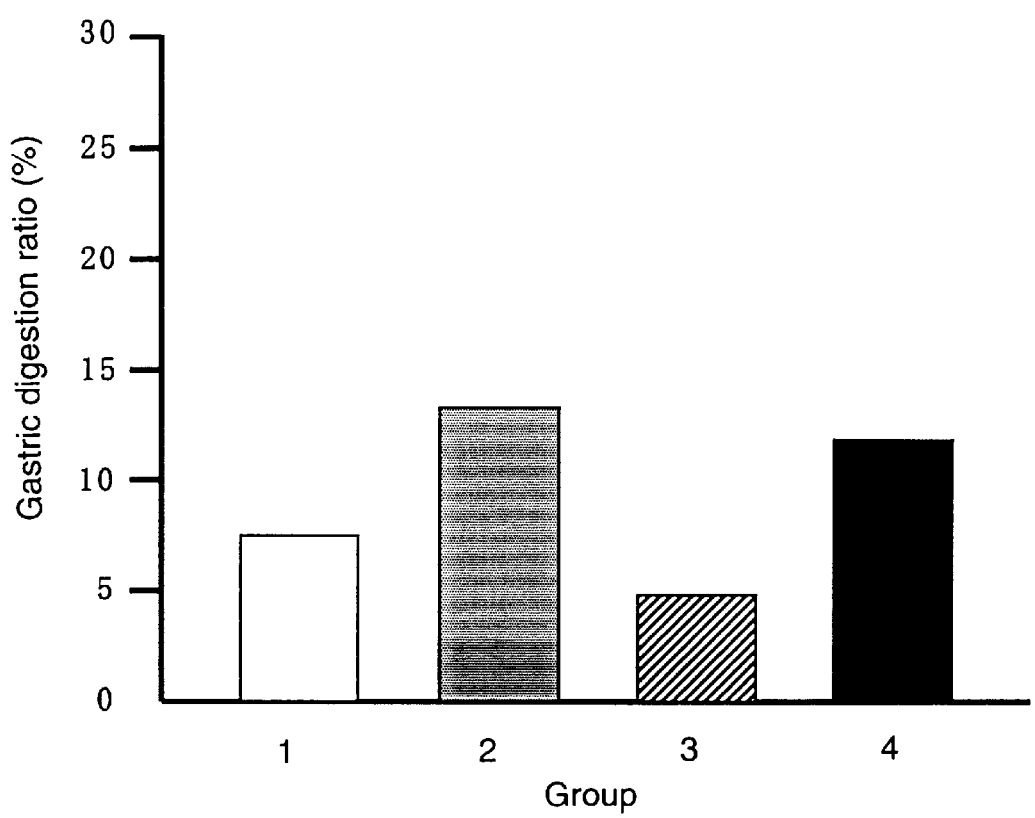
FIG. 14 is a graph showing results after 15 minutes of administration in Example 3.
Figure 15:
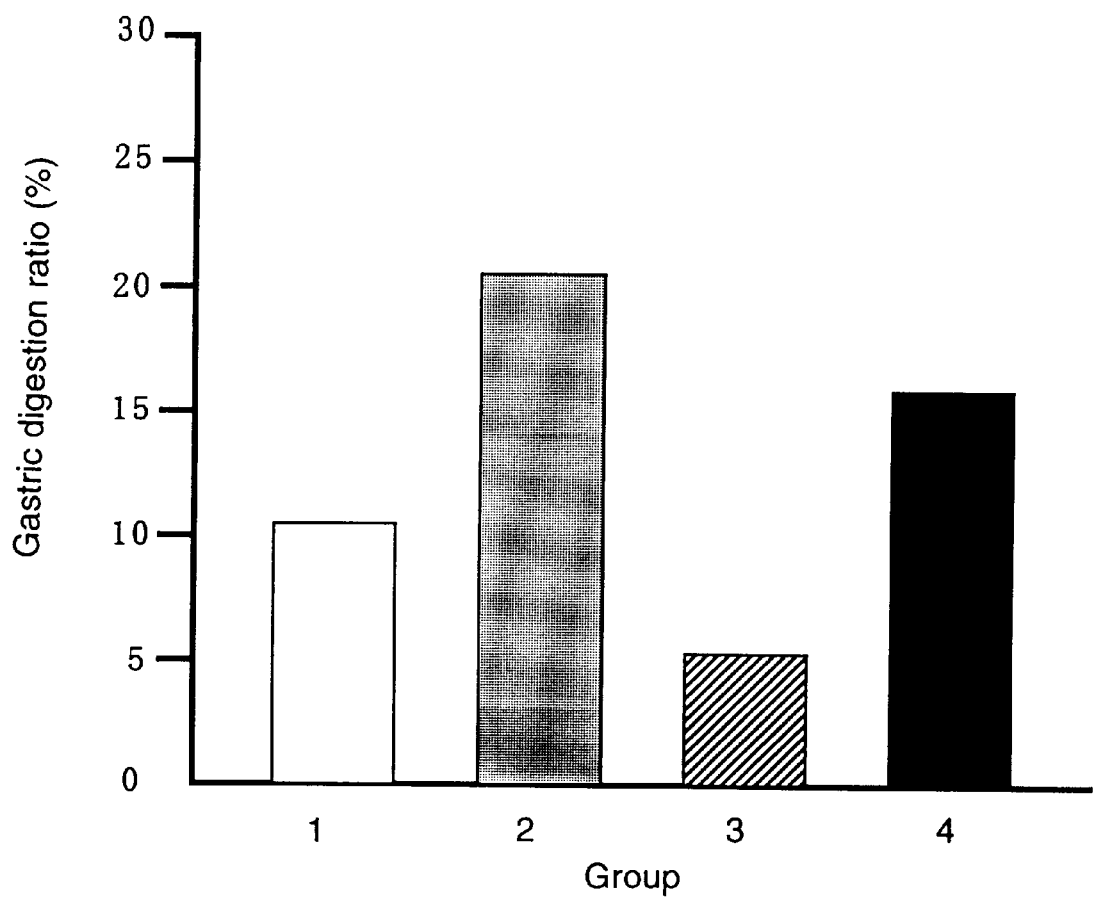
FIG. 15 is a graph showing results after 30 minutes of administration in Example 3.

The symbol * means significant difference at P<0.001,  means significant difference at P<0.01, and * means significant difference at P<0.05. FIG. 12 shows the results after 15 minutes, and FIG. 13 shows the results after 30 minute of the administration in Example 2, and FIG. 14 shows the results after 15 minutes, and FIG. 15 shows the results after 30 minutes of the administration in Example 3.

(2) Results

It is evident that, when ranitidine or famotidine is used in combination with Prozyme 6, the gastric digestion inhibited by ranitidine or famotidine is restored by the joint use of Prozyme 6 similar to the case in Example 1.

Example 4: Joint use of an H, blocker with a multiple digestive enzyme system (1)

The procedure of Example 1 was repeated, except that 15 mg/5 ml/kg of Biodiastase 2000 was orally administered instead of Prozyme 6. The TCA soluble fraction in the stomach was examined by the Folin method in the same manner. Unexpectedly, as a result, it was confirmed that the gastric digestion inhibited by the $H_2$ blocker is evidently prevented by the joint use of the digestive enzyme preparation.

Example 5: Joint use of an $H_7$ blocker with a multiple digestive enzyme system (2)

The procedure of Example 4 was repeated, except that ranitidine was used as an $H_2$ blocker. The TCA soluble fraction in the stomach was examined by the Folin method in the same manner. Unexpectedly, as a result, it was confirmed that the gastric digestion inhibited by the $H_2$ blocker is evidently prevented by the joint use of the digestive enzyme preparation.

Example 6: Joint use of an $H_7$ blocker with a multiple digestive enzyme system (3)

The procedure of Example 4 was repeated, except that famotidine was used as an $H_2$ blocker. The TCA soluble fraction in the stomach was examined by the Folin method in the same manner. Unexpectedly, as a result, it was confirmed that the gastric digestion inhibited by the $H_2$ blocker is evidently prevented by the joint use of the digestive enzyme preparation.

Example 7: Joint use of a PPI with a protease (1) Method

Purified water (control group) or various PPI (omeprazole: 30 mg/kg; lansoprazole: 30 mg/kg; and raveprazole: 20 mg/kg) was administered to seven-week-old Wistar/ST male rats (196.2 to 226.8 g) which were forced to undergo 24 hours of fasting. 60 minutes thereafter, 1.3 g/10 ml/kg of BSA was orally administered as a substrate, and subsequently 60 mg/5 ml/kg of Prozyme 6 was orally administered. Thermally inactivated Prozyme 6 (heated for 20 minutes in boiling water) was used in the control group. After 30 minutes of the administration of BSA, each rat was anesthetized with ether and the stomach excised.

The gastric contents of the excised stomach were transferred to a centrifugation tube and suspended in purified water. The contents in the centrifugation tube were then mixed with 5 ml of 20% trichloroacetic acid (TCA). The mixture was allowed to stand for 30 minutes in an ice bath and was then centrifuged at 3,000 rpm for 20 minutes. The amount of protein in the resulting supernatant fluid, namely the TCA soluble fraction, was measured by the Folin method. The results are summarized in Tables 8 and 9. The gastric digestion ratio was calculated based on the following formula.

TABLE 8

| (Residual digests in the stomach/BSA administered) × 100 | | | | |
|---|---|---|---|---|
|  | Group 1 | Group 2 | Group 3 | Group 4 |
| Number of rats | 5 | 5 | 5 | 5 |
| Dosage (mg) | 253.3 ± 5.2 | 255.0 ± 4.2 | 256.3 ± 3.5 | 252.8 ± 9.3 |
| Digests in the stomach (mg) | 29.4 ± 6.6 | 52.5 ± 9.7 | 18.5 ± 6.6 | 47.3 ± 10.0 |
| Gastric digestion ratio (%) | 11.6 ± 3.1 | 20.6 ± 6.2 | 7.2 ± 2.4 | 18.7 ± 6.5 |
| Gastric pH | 3.5 ± 0.5 | 4.0 ± 0.4 | 5.2 ± 0.5 | 5.5 ± 0.6 |

TABLE 9

|  | Group 5 | Group 6 | Group 7 | Group 8 |
|---|---|---|---|---|
| Number of rats | 5 | 5 | 5 | 5 |
| Dosage (mg) | 256.9 ± 5.3 | 260.0 ± 3.8 | 255.1 ± 4.2 | 254.6 ± 3.9 |
| Digests in the stomach (mg) | 17.3 ± 3.3 | 46.6 ± 9.9 | 18.5 ± 5.5 | 49.9 ± 11.0 |
| Gastric digestion ratio (%) | 6.7 ± 1.9 | 17.9 ± 5.5 | 7.3 ± 1.2 | 19.6 ± 3.1 |
| Gastric pH | 5.3 ± 0.4 | 5.6 ± 0.4 | 5.2 ± 0.4 | 5.5 ± 0.3 |

Figure 16:
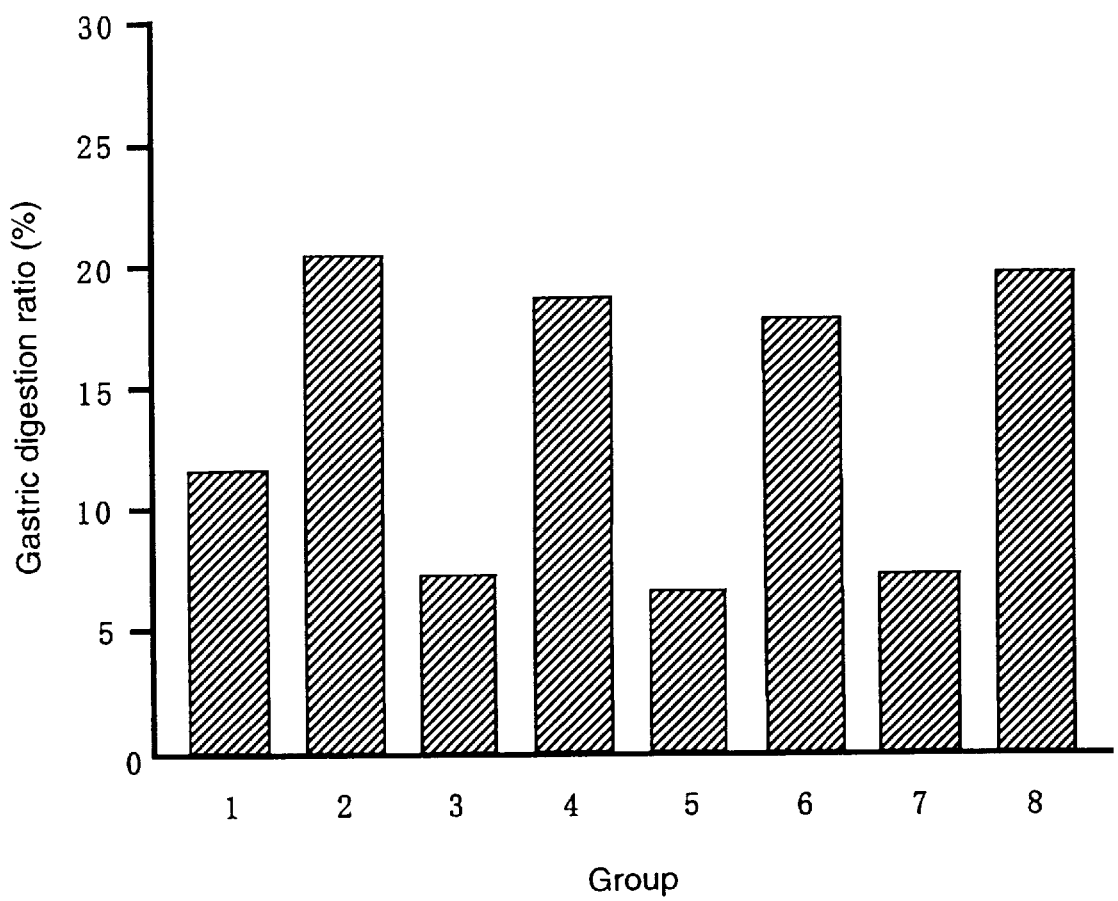
FIG. 16 is a graph showing the result of Example 7.

The individual groups and the ingredients administered to each group in Tables 8 and 9 are as follows.
  Group 1: purified water+heat-inactivated Prozyme 6
  Group 2: purified water+Prozyme 6
  Group 3: omeprazole+heat-inactivated Prozyme 6
  Group 4: omeprazole+Prozyme 6
  Group 5: lansoprazole+heat-inactivated Prozyme 6
  Group 6: lansoprazole+Prozyme 6
  Group 7: raveprazole+heat-inactivated Prozyme 6
  Group 8: raveprazole+Prozyme 6
The above results are shown in FIG. 16.

(2) Result

As is evident from the figures, a single administration of PPI, such as omeprazole, decreases gastric digestion compared to the control group. Most likely this effect occurred because gastric digestion by pepsin is suppressed by omeprazole or like PPIs. On the other hand, when a PPI such as omeprazole was used in combination with Prozyme 6, significant acceleration of gastric digestion was observed compared to the group that received PPI alone. Thus, the digestion inhibited by PPI is prevented.

Thus, unexpectedly, according to the present invention, the gastric digestion of food inhibited by an $H_2$ blocker can be prevented without inhibiting the therapeutic effect for the treatment of ulcers.

While the invention has been described in detail and with reference to specific embodiments thereof, it will be apparent to one skilled in the art that various changes and modifications can be made therein without departing from the spirit and scope thereof.

This application is based on Japanese patent application Hei-9-307832, filed on Oct. 21, 1997, and incorporated herein by reference.

What is claimed is:

1. A pharmaceutical agent consisting essentially of a digestive enzyme and at least one agent selected from the group consisting of histamine $H_2$ receptor antagonists and proton pump inhibitors.

2. The pharmaceutical agent of claim 1, wherein said digestive enzyme is an enzyme that acts at the gastric pH.

3. The pharmaceutical agent according to claim 1, wherein said digestive enzyme is protease.

4. The pharmaceutical agent according to claim 1, wherein said histamine $H_2$ receptor antagonist is at least one compound selected from the group consisting of cimetidine, ranitidine and famotidine.

5. The pharmaceutical agent according to claim 1, wherein said proton pump inhibitor is at least one compound selected from the group consisting of omeprazole, lansoprazole, and raveprazole.

6. A method of treating gastric ulcers comprising the administration of a therapeutically effective dose of a pharmaceutical agent to a host in need of treatment, wherein:

(a) said pharmaceutical agent consisting essentially of a digestive enzyme that acts at the gastric pH, and at least one agent selected from the group consisting of a histamine $H_2$ receptor antagonist and a proton pump inhibitor; and (b) normal digestion in the stomach of said host is maintained.

7. The method of claim 6, wherein said digestive enzyme is a protease.

8. The method of claim 6, wherein said histamine $H_2$ receptor antagonist is at least one compound selected from the group consisting of cimetidine, ranitidine, and famotidine.

9. The method of claim 6, wherein said proton pump inhibitor is at least one compound selected from the group consisting of omeprazole, lansoprazole, and raveprazole.

* * * * *